(12) United States Patent
Martin et al.

(10) Patent No.: US 7,193,114 B1
(45) Date of Patent: Mar. 20, 2007

(54) EXTRACTION OF METALS BY MERCAPTANS ATTACHED TO SILICA GEL BY AZEOTROPIC DISTILLATION

(75) Inventors: Dean F. Martin, Tampa, FL (US); Craig A. Bowe, Tampa, FL (US)

(73) Assignee: University of South Florida, Tampa, FL (US)

( * ) Notice: Subject to any disclaimer, the term of this patent is extended or adjusted under 35 U.S.C. 154(b) by 604 days.

(21) Appl. No.: 10/707,814

(22) Filed: Jan. 14, 2004

Related U.S. Application Data

(60) Provisional application No. 60/319,866, filed on Jan. 14, 2003.

(51) Int. Cl.
C07C 381/00 (2006.01)
C07C 31/34 (2006.01)
(52) U.S. Cl. .......................... 568/62; 568/69; 568/841
(58) Field of Classification Search ................ None
See application file for complete search history.

(56) References Cited

U.S. PATENT DOCUMENTS

| | | |
|---|---|---|
| 5,597,476 A | 1/1997 | Hearn et al. |
| 5,728,854 A | 3/1998 | Chen et al. |
| 5,772,909 A | 6/1998 | Jones et al. |
| 5,807,506 A | 9/1998 | Cunningham et al. |

OTHER PUBLICATIONS

Extraction of Heavy Metals by Amines Adsorbed onto Silica Gel; www.dekker.com/sevlet/product/DOI/101081ESE120024454/section/default; Sep. 8, 2003.
Extraction of Heavy Metals by Mercaptans Attached to Silica Gel by Corkscrew Mechanism; www.dekker.com/servlet/product/DOI/101081ESE120013264/section/default; Aug. 13, 2002.
Craig A. Bowe et al., Extraction of Heavy Metals Using Modified Montmorillonite KSF, Florida Scientist, 2004, 74-79, 67(1).
2004 Meeting Program Issue, Florida Scientist, 2004, p. 46-47, vol. 67.

*Primary Examiner*—Sikarl A. Witherspoon
(74) *Attorney, Agent, or Firm*—Smith & Hopen, P.A.

(57) ABSTRACT

The present invention attaches a molecule that contains a hydroxyl group (OH) attached to a carbon chain which is attached to a coordinating atom or atoms, the acidity of which is greater than that of silica (i.e., pKA <10). The condensation is achieved by mixing silica gel, appropriate amount of ligand, and a drop of conc. sulfuric acid in toluene in a flask attached to a Dean-Stark tube. Heating of the mixture is continued until the amount of water, obtained by azeotropic distillation and condensation, reaches a constant value. Toluene is filtered off, and recycled. The supported ligand is dried under reduced pressure to remove residual toluene. The composite (ligand attached to silica) can then be used by batch or column method to remove heavy metal ions from aqueous solution.

15 Claims, 2 Drawing Sheets

$SiO_2$ + $HOCH_2SH$ =  + $H_2O$

A: $SiO_2-CH_2-SH$ +

2 HX

A: 2 $SiO_2-CH_2-SH$ + $MX_2$
B: $(SiO_2-CH_2-S)_2M$ +

EXTRACTION OF METALS BY MERCAPTANS ATTACHED TO SILICA GEL BY AZEOTROPIC DISTILLATION

CROSS REFERENCE TO RELATED APPLICATION

This disclosure claims benefit of provisional application Ser. No. 60/319,866 entitled: "Azeotropic Attachment of Ligands to Silica Gel for Metal Removal Agents," filed Jan. 14, 2003 by the same inventors.

BACKGROUND OF INVENTION

1. Field of Invention

This invention relates to the removal and filtration of heavy metals from an aqueous solution.

2. Background of Invention

Removal of heavy metals has several applications, including improved analyses, through concentration of metals, economy, remediation, and general concern for eliminating toxic substances from environmental samples or preventing their introduction to the environment. Concentration of metals from dilute aqueous samples would be economically sound for disposal purposes.

In the typical extraction process of a metal from an aqueous solution containing the metal values, the aqueous solution containing the metal values is contacted by a solution of a water insoluble extractant capable of extracting the desired metal, in a water immiscible hydrocarbon solvent. After contact for a sufficient time to extract at least a portion of the metal values, the hydrocarbon solvent phase, now loaded or containing the extracted metal values, is separated from the aqueous solution phase from which the metal values have been extracted, due to the immiscibility of the organic and aqueous phases. The loaded organic phase is then typically contacted with an aqueous stripping solution thereby forming two phases again, (a) an aqueous strip phase, now containing metal values stripped from the organic extractant phase, and (b) an organic phase from which the metal values have been stripped. Again the organic and aqueous phases are separated due to immiscibility of the phases. The metal is then recovered from the metal loaded aqueous strip phase, by conventional means, such as electrowinning, precipitation or other means suitable to the particular metal, generally electrowinning being the preferred recovery means. Both acid and ammoniacal aqueous solutions have been employed as stripping solutions in the past, one commercial process in the recovery of nickel employing an ammoniacal aqueous stripping solution. The organic extractant employed commercially in extraction of metals such as copper, nickel and zinc are the phenolic oxime extractants. In the process, particularly with aldoxime extractants, it is often desirable to include in the organic extractant phase an equilibrium modifier, to provide for the most efficient extraction and "net transfer" of the metal being recovered. In the process there is a transfer of metal in the extraction stage from the aqueous feed solution to the organic extractant phase, followed by a second metals transfer from the organic phase to the aqueous strip solution phase, the two metal transfers representing the "net metal transfer" of the process. Effectively "net transfer" can be determined by observing the difference between the extraction isotherms and the strip points. Typically equilibrium modifiers employed with the phenolic oxime extractants in the process have generally been various alcohols and esters. However, this process results in significant amounts of ammonia required for loading along with metal values into the organic phase. The ammonia must then be removed from the organic phase, with a high cost of ammonia, system costs and acid costs required to neutralize the ammonia carried in the organic phase by a scrub section.

U.S. Pat. No. 5,728,854 describes a method for separating iron from nickel and/or cadmium contained in a battery waste where the first step in which the spent batteries are crushed and calcined. The calcined pieces are mixed with an acetic acid aqueous solution before acetic acid and water are removed by evaporation or distillation so as to produce a residue containing metallic acetates. Water, the residue and an oxidant are mixed such that Fe+ and Fe++ acetates are converted into a basic ferric acetate, $Fe(CH_3COO)_2OH$, which is insoluble in water and is recovered by filtration.

Supported coordinating agents are also used for metal-ion removal. The method provides favorable equilibria for removal, together with the co-advantages of convenience and ease of separation. Supported coordinating agents afford the possibility of design of ligands for specific applications, both in the selection of the ligands to be used for given types of metals (calcophiles, with an affinity for sulfur, or lithophiles with an affinity for oxygen donors, etc). Supports include several polymeric systems which are available. Polystyrene impregnated with $\beta$-diphenylglyoxime is a selective reagent for palladium. Treated foam is used as a support for coordinating agents. Ion-exhange resins are used as supports for those coordinating agents that can be derivatized or converted to ions. Attachment of the ligand to the substrate through derivatization is effective, using 3-chloropropyltrimethoxysilane as a means of attaching polyamines to silica gel. Such derivatization, however, means an additional step and at an additional cost.

Azeotropic distillation has been used for solvent removal, as described in on U.S. Pat. No. 5,807,506, which describes a process for the preparation of conductive polymers which comprising (a) mixing at least one monomer with at least one conductive component, solvent, at least one polymerization initiator, and an optional chain transfer component; (b) effecting solution polymerization by heating; (c) removing the solvent by azeotropic distillation in an aqueous phase to generate a mixture of polymer and conductive component; (d) drying and grinding the resulting mixture; thereafter dissolving the product resulting in at least one monomer, at least one initiator, and at least one crosslinking component, and an optional chain transfer agent to form an organic phase; (e) mixing said organic phase with a second aqueous phase comprised of water, stabilizer, and an alkali halide; (f) polymerizing the resulting suspension by heating; and (g) subsequently optionally washing and drying the polymeric product, and which product is comprised of polymer and conductive component dispersed therein. However, this method, although employs the azeotropic distillation to remove the solvent, is not applicable in removing metals from aqueous solutions.

U.S. Pat. No. 5,772,909 describes separation of vanillin from second organic chemicals by azeotropic distillation using as an effective azeotropic distillation agent, dibenzyl ether. Vanillin is difficult to separate from second organic chemicals produced therewith, such as parahydroxy-benzaldehyde by conventional distillation or rectification because of the proximity of their boiling points. This reference, although providing an azeotropic distillation method to remove agents from aqueous solutions, does not address the removal of heavy metals.

U.S. Pat. No. 5,597,476 describes catalytic cracked naphtha, desulfurized with minimum loss of olefins and octane.

The naphtha is fed to a first distillation column reactor which acts as a depentanizer or dehexanizer with the lighter material containing most of the olefins and mercaptans being boiled up into a first distillation reaction zone where the mercaptans are reacted with diolefins to form sulfides which are removed in the bottoms along with any higher boiling sulfur compounds. The bottoms are subjected to hydrodesulfurization in a second distillation column reactor where the sulfur compounds are converted to H.sub.2 S and removed. The lighter fraction containing most of the olefins is thus not subjected to the harsher hydrogenation conditions of the second reactor. However, this reference also does not address the removal of metals from aqueous solutions with the use of mercaptans attached to a substrate.

Thus, what is needed is an improved method of removing heavy metals from aqueous solutions which is inexpensive, reliable and simple, along with applicability to variety of substrates. Nothing in the prior art including the aforementioned references implicitly or explicitly discloses the present invention covering the removal of metals, or heavy metals by mercaptans attached to silical gel by azeotropic distillation. Furthermore, nothing in the prior art discloses the products produced by such methods.

SUMMARY OF INVENTION

A method for removing metals from aqueous solutions is described, specifically by azeotropic attachment of mercaptans to silica gel, comprising the steps of condensing a mixture of silica gel and a mercapatan in alcohol solution by heating the mixture, until a constant value is attained for water vapor, which is generated during the heating, and a resulting composite is then obtained to form an azeotropic mixture. Finally, the heavy metal ions are removed from an aqueous solution by azeotropic distillation.

Azeotropic distillation is a process for separating by distillation, products not easily separable otherwise. The essential characteristic of the process is the introduction of another substance which then forms an azeotropic mixture, with one or sometimes both initial substances but using only small quantities, then is distilled off leaving the pure product.

Advantages of the present invention include: (1) it is an inexpensive method of attachment; (2) the process is completed in three simple steps; (3) it is a convenient, reliable method for showing extent of reaction; (4) it is applicable to variety of substrates, silica gel being most common; (5) other substrates include clays (attapulgite and montmorillonite) are covered; (5) the process also works with magnetic iron oxide, giving a product that can be subjected to magnetic separation; (6) the process is applicable to a range of ligands including CH2CH2SH, which favors removal of heavy metals like lead, copper, silver, cadmium; (7) the process is applicable to an amine ligand —CH2CH2N(CH3)2; (8) the process enables removal of metals subject to pH control; (9) the end product will not affect benign ions (sodium, potassium, magnesium, and calcium); and (10) the end product is thermally stable to 110 degrees Celsius.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
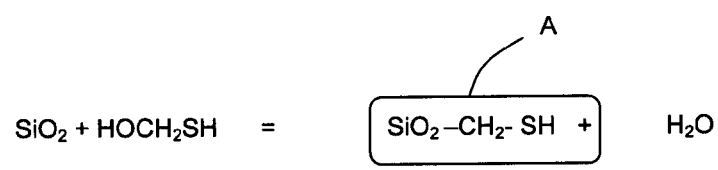
FIG. 1 shows the reaction of 2-mercaptoethanol and silica gel.

As used in this application, the following terms shall have the meanings described:

Mercapatans:

Also referred to as ligand in the present application. Mercaptans have the general formula RSH. They form salts with sodium, potassium and mercury, and are formed by warming alkyl halides or sulphates with potassium hydrosulphide in concentrated alcoholic or aqueous solution. The present experiment uses ethanol, specifically 2-mercaptoethanol, having a formula of $C_2H_6OS$, and molecular weight of 78.13, a boiling point of 430.2 K, and the following chemical structure:

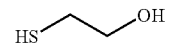

Azeotropic mixture: Liquid compounds whose boiling point, and hence composition, does not change as vapor is generated and removed on boiling. The boiling point of the azeotropic mixture may be lower or higher than those of its components.

Azeotropic distillation: A separatory distillation of a liquid in which a substance is added to the distilland mixture in order to assist separation of its components by forming with one or more of the components a mixture having a minimum boiling point. The art has also used the term for a distillation process in which two substances in the starting material are removed by their forming a minimum boiling mixture.

Coordinating agent: A chemical agent which combines with unwanted metal ions, and promotes excretion of such metals.

An economical approach is introduced, by the inventors of the present application, using silica support, using a ligand with a long-chain hydrocarbon. The method consists of filling silica gel pores with hexane that the hydrocarbon moiety would be soluble in and would presumably exist in a stretched configuration. Removing the hexane by evaporation, leads to the hydrocarbon chain in the pore to coil upon itself to minimize effects of hydrophobicity, caused by exposed hydroxy groups lining the pores. A corkscrew configuration may be used with two-three turns per chain of 12 carbons. The coil causes the hydrocarbon moiety to be wedged into the pores.

N-dodecylbenzoylacetone, loaded onto silica gel removes 99.9% of available aqueous copper in a single-pass method. Sorption accounts for considerable fraction of the removal of copper, depending on the pH using LIX® 54 (n-dodecylbenzoylacetone), oleoylacetone, or n-dodecylsalicyldoximine. Similar results are obtained for removal of cadmium from aqueous solutions. N, N' didodecyldithiooxamide supported on silica gel is effective in removing aqueous copper (99.1+0.3%), nickel (70.7+0.1.7%), and silver (83.5+0.7%) near neutral pH.

These methods are concerned with the effectiveness of mercaptans of varying chain lengths loaded onto silica gel in removing aqueous heavy metals, using normal mercaptans with chain lengths from six to 18 carbons. Under optimal conditions, essentially quantitative removal is achieved for Cd, and about 80% removal for Cu, Pb, Ni. The presently claimed method looks at an alternative approach of attaching a mercaptan: condensation of silica gel with 2-mercaptoethanol.

The present invention first attaches a molecule that contains a hydroxyl group (OH) attached to a carbon chain which is attached to a coordinating atom or atoms, the acidity of which is greater than that of silica (i.e., pKA <10). The condensation is achieved by mixing silica gel, appropriate amount of ligand, and a drop of concentrated sulfuric acid in toluene in a flask attached to a Dean-Stark tube. Heating of the mixture is continued until the amount of water, obtained by azeotropic distillation and condensation, reaches a constant value. Toluene is filtered off, and recycled. The supported ligand is dried under reduced pressure to remove residual toluene. The composite, the ligand attached to silica, can then be used by batch or column method to remove heavy metal ions from aqueous solution.

Experiment

2-Mercaptoethanol is obtained from Fisher Scientific and is used without further purification. Activated silica gel (20 g) is treated with 50 mL of toluene dried with 2 g of anhydrous sodium sulfate. The mixture is transferred to a 500 mL flat bottom flask that is fitted with Dean-Stark trap and a condenser. Then, the Dean-Stark trap is filled with toluene. A solution of 0.1 mole of 2-mercaptoethanol dissolved in 50 mL of anhydrous toluene is added to the silica gel mixture, and the reaction mixture is agitated under reflux, 120° C., on a magnetic stirrer hot plate for two hours. Upon cooling the solid is separated by filtration, dried under vacuum, and used for analyses.

Metal analyses are obtained using a Varian SpectrAA 100 atomic absorption spectrometer coupled to a Dell computer and Hewlett Packard 550 printer. Five standards, prepared by serial dilution, are used to determine the calibration plot. The spectrometer determines the concentration of the given metal, the concentration of which does not exceed 10 ppm, by the calibration curve. Calibrations are performed each time an analysis is made, and a total of five samples are used to calibrate the instrument.

Solutions of 1.57 mM of lead(II) nitrate, cadmium(II) acetate, and copper(II) nitrate are prepared in 1.0-L volumetric flasks. Five 100-mL aliquots of stock solution are analyzed using an excess of 2-mercaptoethanol-silica gel composite, of 4 g, which is added to each metal solution, and the resulting mixture is agitated in a New Brunswick Scientific Company Model G76 gyrotory water bath shaker for a period of two hours (200 rpm).

The reaction of 2-mercaptoethanol and silica gel is shown in FIG. 1, where A is a representation of silica gel-ligand composite. The metal removal procedure is summarized in FIG. 2, where B is a representation of the metal-containing product.

The following results in Table I, indicate that it is possible to remove more than 90% of three heavy metals from aqueous solutions using silica-ligand composites with a removal of aqueous copper(II) nitrate using excess 2-mercaptoethanol, providing an average removal of 92.1%. With an excess of silica-supported 2-mercaptoethanol, the removal of copper ion from solution is achieved with significant success. Removal of lead from aqueous lead(II) nitrate using 2-mercaptoethanol provides an average removal of 91.2%. Removal of cadmium from aqueous cadmium acetate provides an average removal of 92.8%.

TABLE 1

The removal of divalent metal ions using 2-mercaptoethanol attached to silica gel from 0.00157 M Solution.

| Divalent Metal | Silica Supported Reagent | % Extraction |
| --- | --- | --- |
| $Cu^{2+}$ | 2-mercaptoethanol | 92.1 ± 1.2 |
| Control | | 18.3 ± 5.1 |
| $Pb^{2+}$ | 2-mercaptoethanol | 91.2 ± 0.3 |
| Control | | 28.8 ± 14.2 |
| $Cd^{2+}$ | 2-mercaptoethanol | 92.8 ± 0.5 |
| Control | | 13.2 ± 2.6 |

Based on these t-tests performed, there is no statistically significant difference in the removal percentage among the studied divalent metals using equal amounts of 2-mercaptoethanol.

Figure 3:
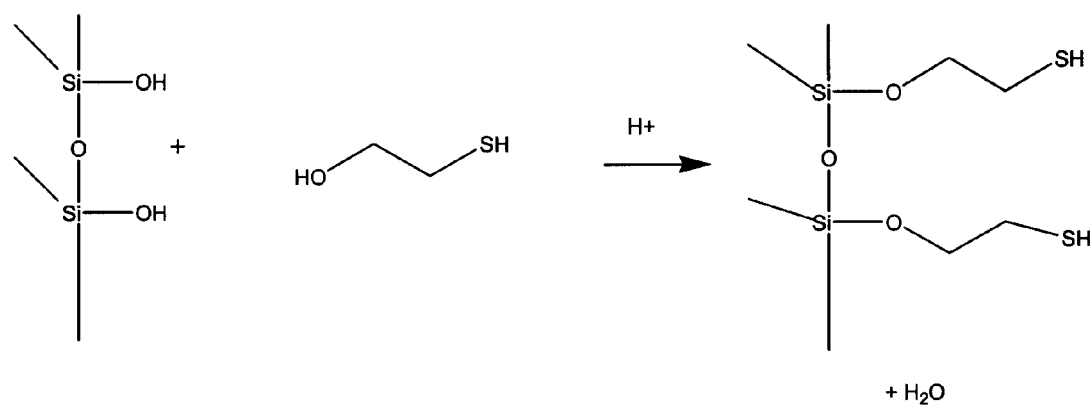
FIG. 3 is a condensation reaction between a silica gel surface and a bifunctional compound.

The Dean-Stark apparatus, as used in the present experiment, is used in a variety of condensation reactions involving organic compounds. The esterification reaction, in which water is lost as a product, is a notable and common example of the use of the Dean-Stark apparatus as part of a synthetic protocol. Silica surfaces slightly acidic, with pKa of about 10, can thus facilitate reactions that involve acid catalysis. The silica gel surface can facilitate a condensation reaction between itself and a bifunctional compound such as a mercaptoalcohol, as shown in FIG. 3. The synthesis of modified silica gel using 2-mercaptoethanol with a Dean-Stark trap apparatus is shown in FIG. 3. Further, with the constant removal of water, as shown in FIG. 1, the otherwise reversible reaction is driven to completion, and a high yield of composite product A may be expected.

The removal of the metals by distillation, after the composite of the azeotropic mixture has been obtained, may be one of several processes that are known in the art. For example, one process is described by George C. Blytas in "Chemical Engineering Communication", 1990, Vol. 88, pp. 127–151, under the title "Continuous countercurrent solid-liquid contacting in rotary disc contactors". A column with discs placed above one another is described in this article. The force of gravity causes solid particles of resin to fall from the top to the bottom of the column and to absorb benzene from an upward-flowing supply stream. Situated between the perforated plates are siring elements which rotate at high speed in order to suspend the particle material.

Other distillation processes include methods where the particle material for extraction and the extraction agent are in a number of successive vessels, the vessels with particle material being conveyed batchwise in a certain direction and the extraction agent being pumped in the opposite direction from one vessel to the next. The particle material gradually loses the above-mentioned component, and the extraction agent takes up said component. The bed of particle material stops in each vessel and the liquid extraction agent flows through it. Although on a macro scale this can be described as a countercurrent process, on a micro scale there is no question of countercurrent here.

Components from solid particle material may also be removed by extraction, where a column is used with one or more tubes which extend between the ends of the column, at least one filter being fitted in the wall of each tube. The particle material is fed in at a first end of the column and, forced by hydraulic pressure, moves along the extending tubes to a scraper fitted at the second end of the column. Extraction liquid is fed into the column at the second end and flows in countercurrent to the particle material in the direction of the first end of the column. Extraction liquid with component from the particle material dissolved in the extraction liquid passes by way of the filters into the tubes and flows in countercurrent to the particle material to an outlet at the first end. The particle material is the scraped off at the second end.

For a polydentate ligand such as a coordinating agent, and for bivalent metal ions, there is a fixed order of stabilities: Mn<Fe <Co<Ni<Cu>Zn. Also known as the Irving-Williams Order. The available data justifies including other metals in a series of relative stabilities or coordinating tendencies: Pd>Hg>UO2>Be>Cu>Ni>Co>Pb>Zn>Cd>Fe>Mn>Mg>Ca>Sr>Ba. Generally, the ligands of the available data as indicated here involves oxygen or nitrogen types, and some deviation may be expected for ligands with sulfur donors.

Figure 2:
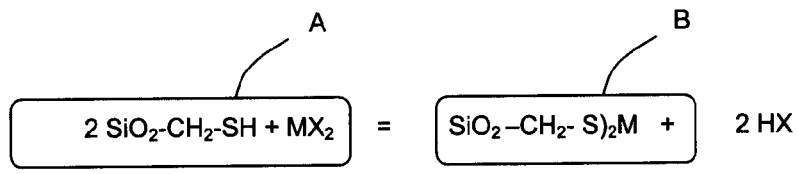
FIG. 2 shows the metal removal procedure.

In the experimentation of removing metals, which represent an equilibrium, as shown in FIG. 2, there is no effort to "force" the reaction by adding base as shown in FIG. 1, to shift the equilibrium. Instead, the reaction depends upon the availability of the counter-ion, acetate, a weak base to assist the shift of the equilibrium. Thus, the maximum removals are related to the relative chelating or coordinating tendencies and are expected to follow the extended order.

The metals and their maximum removals are: Cu (92.1%), Pb (91.2%) and Cd (92.8%). The enhanced removal percentages are obtained using added base, although this adds to the cost for an actual process. Of the three metals examined, cadmium proves to be the most successfully removed, which may be expected from the extended order. Cadmium is also a calcophile and coordination with sulfur donors are favored. Heavy metal removal using 2-mercaptoethanol attached to silica gel is achieved with a great degree of success. The removal effectiveness is independent of the type of metal used.

Use of silica-supported mercaptalcohols, using a Dean-Stark trap, affords a relatively inexpensive method for providing convenient method of effective removal of selected heavy metal ions and the application to other ligands should be considered. An alternative, typically used is derivatization by a silicon reagent, e.g. 3-chloropropyltrimethoxysilane, which requires the use of an additional reagent, which adds to the cost of the process, and introduces the need for disposal of product. The process used here, produces innocuous water, and the amount gives a measure of the extent of the reaction. The conversion presently is quantitative.

The nature of the ligand may be varied and multidentate ligands could be used, provided one end is an alcohol and the other terminus is not a moiety that would condense with silica gel. A potential ligand of the type HO Y-Z could also be used, provided the donor moiety has certain characteristics. For example, the acidity of Z must be greater than that of silica gel, or suitable blocking agents must be available to prevent condensation at the wrong end.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there-between. Now that the invention has been described,

The invention claimed is:

1. A method of removing metals from aqueous solutions comprising the steps of:
   condensing a mixture of silica solution and mercapatan in alcohol solution by heating the mixture, with a constant removal of water by vapor generated during the heating, wherein a resulting composite is obtained to form an azeotropic mixture; and
   removing heavy metal ions from an aqueous solution by distillation.

2. The method of claim 1, wherein the step of condensing is performed by Dean-Stark apparatus.

3. The method of claim 1, wherein the step of removing metal ions is performed by evaporation.

4. The method of claim 1, wherein the mercaptan is 2-mercaptoethanol.

5. The method of claim 1, wherein the mercaptan is a coordinating agent.

6. The method of claim 1, wherein the step of condensing is obtained by agitating mixture on a hot plate and then cooling the mixture.

7. The method of claim 1, wherein the heavy metal ions which are removed, are selected from group consisting of copper, lead and cadmium.

8. The method of claim 1, wherein the step of removing metals, incorporates acetate to shift equilibrium and obtain a greater percentage removal of metal ions.

9. The method of claim 1, wherein the step of condensing, further comprises adding toluene to the mixture.

10. The method of claim 9, wherein the toluene is filtered off and recycled after heating and agitating the mixture.

11. The method of claim 1, wherein the mercaptan in alcohol solution has a greater acidity than the silica gel.

12. A method of azeotropic attachment of mercaptans to silica gel for metal-removing agents comprising the steps of:
   heating a mixture of silica gel, a mercapatan in alcohol solution, and toluene, until a constant value is attained for water vapor, obtained by azeotropic distillation, wherein a resulting composite is obtained forming an azeotropic mixture;
   condensing the mixture by cooling; and
   removing heavy metal ions from an aqueous solution by distillation.

13. The method of claim 12, wherein the mixture further comprises sodium sulfate.

14. A method of azeotropic attachment of mercaptans to silica gel for metal-removing agents comprising the steps of:
   adding silica gel, a mercapatan in alcohol solution, toluene and sodium sulfate to form a mixture;
   agitating the mixture on a hot plate, thereby concurrently heating the mixture, until a constant value is attained for water vapor, which is generated during the heating, condensing the mixture by cooling, wherein a resulting composite is obtained to form an azeotropic mixture; and
   removing heavy metal ions from an aqueous solution by azeotropic distillation.

15. The method of claim 14, wherein after the step of condensing, the toluene is filtered off and recycled.

* * * * *